United States Patent
Shimura et al.

(10) Patent No.: US 9,851,548 B2
(45) Date of Patent: Dec. 26, 2017

(54) OPTICAL MICROSCOPE DEVICE AND TESTING APPARATUS COMPRISING SAME

(75) Inventors: Kei Shimura, Tokyo (JP); Tetsuya Niibori, Tokyo (JP); Mizuki Oku, Tokyo (JP); Naoya Nakai, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 727 days.

(21) Appl. No.: 14/240,323

(22) PCT Filed: Jul. 19, 2012

(86) PCT No.: PCT/JP2012/068300
§ 371 (c)(1),
(2), (4) Date: Feb. 21, 2014

(87) PCT Pub. No.: WO2013/027514
PCT Pub. Date: Feb. 28, 2013

(65) Prior Publication Data
US 2014/0210983 A1     Jul. 31, 2014

(30) Foreign Application Priority Data

Aug. 23, 2011  (JP) ................. 2011-181633

(51) Int. Cl.
*H04N 7/18* (2006.01)
*G02B 21/36* (2006.01)
(Continued)

(52) U.S. Cl.
CPC ....... *G02B 21/361* (2013.01); *G02B 21/0016* (2013.01); *G02B 21/06* (2013.01);
(Continued)

(58) Field of Classification Search
CPC .... H01J 37/28; H01J 37/224; G01N 21/6458; G02B 21/24
(Continued)

(56) References Cited

U.S. PATENT DOCUMENTS

2003/0038931 A1* 2/2003 Toyoda ................. G03B 27/54
355/67
2003/0094586 A1   5/2003 Kurosawa et al.
(Continued)

FOREIGN PATENT DOCUMENTS

JP    2000-089129 A    3/2000
JP    2003-068604 A    3/2003
(Continued)

OTHER PUBLICATIONS

International Search Report issued in International Application No. PCT/JP2012/068300 dated Oct. 16, 2012.
Japanese Notice of Reasons for Rejection, w/ English translation thereof, issued in Japanese Patent Application No. JP 2011-181633 dated Jun. 10, 2014.

*Primary Examiner* — William C Vaughn, Jr.
*Assistant Examiner* — Daniel Tekle
(74) *Attorney, Agent, or Firm* — McDermott Will & Emery LLP

(57) ABSTRACT

The present invention allows observation or capturing of a high-contrast image of a sample for which sufficient contrast cannot be obtained in bright-field observation, such as a wafer having a pattern with a small pattern height. According to the present invention, a sample is illuminated through an objective lens used for capturing an image, and an imaging optics are provided with an aperture filter so that an image is captured while light of bright-field observation components is significantly attenuated.

7 Claims, 15 Drawing Sheets

(51) Int. Cl.
*G02B 21/00* (2006.01)
*G02B 21/10* (2006.01)
*G02B 21/06* (2006.01)
*G01N 23/22* (2006.01)

(52) U.S. Cl.
CPC ......... *G02B 21/10* (2013.01); *G01N 23/2206* (2013.01); *G02B 21/365* (2013.01)

(58) Field of Classification Search
USPC .......................................................... 348/80
See application file for complete search history.

(56) References Cited

U.S. PATENT DOCUMENTS

| | | |
|---|---|---|
| 2004/0174512 A1 | 9/2004 | Toyoda et al. |
| 2008/0151234 A1 | 6/2008 | Imai et al. |
| 2010/0053584 A1 | 3/2010 | Kajiyama et al. |

FOREIGN PATENT DOCUMENTS

| | | |
|---|---|---|
| JP | 2003-149169 A | 5/2003 |
| JP | 2004-101406 A | 4/2004 |
| JP | 2005-049663 A | 2/2005 |
| JP | 2007-026885 A | 2/2007 |
| JP | 2008-166320 A | 7/2008 |
| JP | 2010-062281 A | 3/2010 |

\* cited by examiner

OPTICAL MICROSCOPE DEVICE AND TESTING APPARATUS COMPRISING SAME

RELATED APPLICATIONS

This application is the U.S. National Phase under 35 U.S.C. §371 of International Application No. PCT/JP2012/068300, filed on Jul. 19, 2012, which in turn claims the benefit of Japanese Application No. 2011-181633, filed on Aug. 23, 2011, the disclosures of which Applications are incorporated by reference herein.

TECHNICAL FIELD

The present invention relates to an optical microscope device for observing or capturing a high-contrast image of a sample, which has low contrast in bright-field observation and is difficult to observe, and an inspection apparatus having the same.

BACKGROUND ART

When using an inspection apparatus for inspecting semiconductor wafers or other samples using light beams or charged particle beams, it is necessary to, when a sample (e.g., a semiconductor wafer) to be inspected is mounted on an inspection stage, accurately determine the rotation about the normal line of the sample plane as the rotation axis and the positions of orthogonal two axes on a plane that is parallel with the sample plane (i.e., perform alignment).

In conventional devices (e.g., see Patent Literature 1), alignment is performed by capturing an image of a specific pattern located at a plurality of positions on a sample using a low-magnification optical microscope, and rotating and/or translating the sample so that the specific pattern appears at a predetermined position. A bright-field optical microscope is used for the optical microscope. In order for a specific pattern to be recognized from the captured image, the specific pattern should have high contrast with the background.

CITATION LIST

Patent Literature

Patent Literature 1: JP 2008-166320 A
Patent Literature 2: JP 2003-149169 A

SUMMARY OF INVENTION

Technical Problem

With reductions in the size of patterns in recent years, it has become difficult to secure sufficient contrast of patterns on the captured images for use in alignment. Consequently, a problem would arise that pattern recognition fails, resulting in an alignment failure. This is partly considered to be due to a reduction in the thickness of a resist film deposited in a lithography step or a conductor or a semiconductor material for forming a device. With a reduction in the film thickness, height of a pattern formed on the resist film, or a pattern formed through etching on the conductor or the semiconductor material has become smaller than one tenth of the wavelength of visible rays used for capturing an image of the pattern. Consequently, it has become difficult to secure sufficient contrast of patterns when using some bright-field optical microscopes.

As a measure against a shortage of contrast, using pattern enhancement, which is conducted through image processing, or edge enhancement, which is conducted through dark-field observation using a bright/dark field objective lens, is considered. However, the former has a problem in that a pattern is difficult to recognize since noise of the image is also emphasized. Meanwhile, the latter has a problem in that the brightness of the captured image is insufficient due to the low illumination efficiency; thus, alignment can be performed only after lowering the throughput by taking a long time for capturing an image. Further, the latter needs a thick objective lens. The presence of such an objective lens becomes a constraint in mounting the optical microscope on an inspection apparatus for inspecting samples such as semiconductor wafers, and thus can result in a problem of an increased size of the apparatus.

The present invention has been made in view of the foregoing problems, and provides a compact optical microscope device that can stably obtain a pattern image of even a sample, which has a pattern with a small pattern height, with sufficient contrast, and an inspection apparatus having the same.

Solution to Problem

According to the present invention, a sample is illuminated through an objective lens used for observing or capturing an image, and an imaging optics is provided with an aperture filter so that an image is captured while light of bright-field observation components is significantly attenuated.

Advantageous Effects of Invention

According to the present invention, it is possible to stably obtain a pattern image of even a sample, which has a pattern with a small pattern height and thus cannot have sufficient contrast in bright-field observation, with sufficient contrast. Other problems, configurations, and advantageous effects will become apparent from the following description of embodiments.

DESCRIPTION OF EMBODIMENTS

Hereinafter, embodiments of the present invention will be described with reference to the drawings. It should be noted that embodiments of the present invention are not limited to those described below, and various variations are possible within the spirit and scope of the present invention.

[Device Configuration 1]

Figure 1:
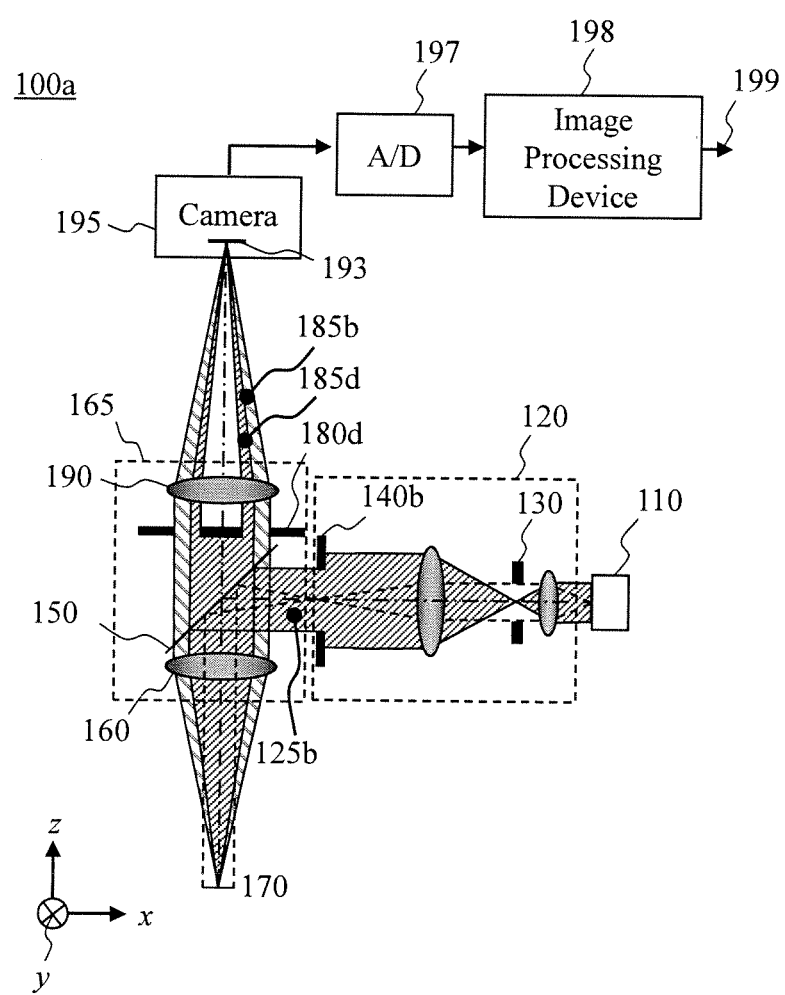
FIG. 1 shows the schematic configuration of an optical microscope device.

FIG. 1 shows the schematic configuration of an optical microscope device 100a in accordance with an embodiment. FIG. 1 represents a device that captures an image by illuminating a sample through epi-illumination and acquiring a reflected beam from the sample.

The optical microscope device 100a includes an illumination light source 110, an illumination optics 120, an imaging optics 165, a camera 195, an A/D converter 197, and an image processing device 198, and outputs an image 199 of a sample mounted on an object plane 170 of the imaging optics 165.

For the illumination light source 110, a halogen lamp, a metal halide lamp, a mercury lamp, a xenon lamp, or the like is used. It should be noted that a light guide may also be used to guide an illumination beam from the illumination light source 110 to the illumination optics 120. Further, a light emitting diode (LED) or a laser diode (LD) may also be used for the illumination light source 110. A light beam radiated from the illumination light source 110 is caused to irradiate the sample mounted on the object plane 170 of the imaging optics 165 via the illumination optics 120, a beam splitter 150, and an objective lens 160.

The illumination optics 120 includes an illumination lens, a field stop 130 arranged at a position that is conjugate to the sample plane, and an aperture filter 140b of the illumination optics that is arranged on the pupil plane of the objective lens 160. A light beam reflected by the sample is guided to an image sensor 193 of the camera 195 via the imaging optics 165.

The imaging optics 165 includes the objective lens 160, the beam splitter 150, an aperture filter 180d of the imaging optics, and an imaging lens 190. The aperture filter 180d of the imaging optics is arranged on the pupil plane of the objective lens 160, that is, at a position that is conjugate to the aperture filter 140b of the illumination optics. For the beam splitter 150, a planar element, which has a thin film with uniform transmittance distribution on the surface, or a cubic element, which has a thin film with uniform transmittance distribution inside, is used.

For the image sensor 193 of the camera 195, a CCD area sensor with two-dimensionally arranged pixels is used. However, it is also possible to use a linear sensor with linearly arranged pixels, such as a CCD linear sensor or a TDI (Time Delay Integration) sensor, while moving a sample to acquire a two-dimensional image. The form of the image sensor 193 may be a CMOS sensor, a photo diode array, or the like. An image signal that has been photoelectrically converted by the camera 195 is converted into a digital signal by the A/D converter 197, and is then transmitted to the image processing device 198. The image processing device 198 executes image processing, such as gray scale conversion or a noise reduction process, and outputs the finally obtained image 199.

[Structures of Aperture Filters]

Figure 2A:
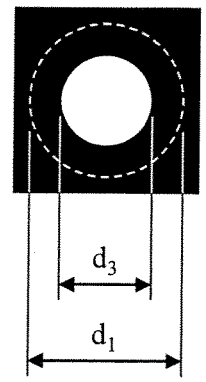
FIG. 2A shows the structure of one of a pair of aperture filters that is suitably installed on an optical microscope device.
Figure 2B:
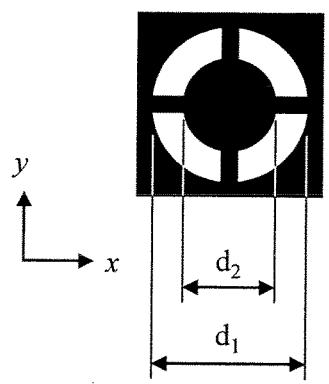
FIG. 2B shows the structure of the other of the pair of aperture filters that is suitably installed on an optical microscope device.
Figure 3:
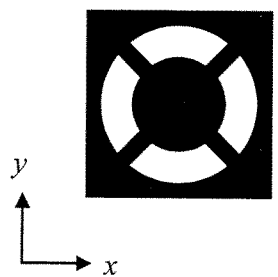
FIG. 3 shows another structure of an aperture filter that is suitably installed on an optical microscope device.

FIGS. 2A, 2B, and 3 each show an exemplary structure of a pair of the aperture filters 140b and 180d used in the optical microscope device 100a. It should be noted that the pair of aperture filters is formed with the aperture filter shown in FIG. 2A and the aperture filter shown in FIG. 2B, and another pair of aperture filters is formed with the aperture filter shown in FIG. 2A and the aperture filter shown in FIG. 3.

FIG. 2A shows an example of the aperture filter 140b used in the illumination optics 120. The aperture filter shown in FIG. 2A has a circular aperture at the center. Provided that the diameter of the pupil of objective lens 160 is d1, the aperture filter 140b has transmission characteristics: a transmittance of 100% within the aperture with a diameter d3 that is smaller than d1, and a transmittance of 0% (light shielding) on the outer side thereof. When the aperture filter 140b with such a structure is used, illumination with a coherence factor of σ=d3/d1 (<1) is realized. When a light beam around the optical axis is used for illumination as described above, it is possible to easily obtain a uniform intensity distribution of an illumination beam on the object plane 170, and thus obtain an image whose brightness at an end of the visual field decreases only to a small degree. Therefore, the structure of the aperture filter 140b is suitable to secure a high recognition rate in pattern recognition during image processing.

FIG. 2B shows an example of the aperture filter 180d of the imaging optics 165. Provided that the diameter of the pupil of the objective lens 160 is d1, the aperture filter 180d has transmission characteristics: a transmittance of 100% within an annular aperture, which is interposed between a circle with the diameter of d1 and a circle with a diameter d2 that is smaller than d1, and a transmittance of 0% (light shielding) on the outer side of the circle with the diameter of d1 and on the inner side of the circle with the diameter of d2. In this specification, an aperture filter with such an annular aperture is also referred to as an "annular aperture filter." In this embodiment, the aperture filter 180d is produced with a thin plate material, adopting a structure in which a circular light-shielding member with the diameter of d2 at the central portion is supported by the outer side thereof from four directions. Therefore, only the portions where support portions are formed have a transmittance of 0% (light shielding) even in the region between the circle with the diameter of d1 and the circle with the diameter of d2. It should be noted that in FIG. 2B, the support members are formed in parallel with the x-axis and the y-axis.

This embodiment shows an example in which the diameter d3>the diameter d2. When such a condition is satisfied, part of the components of an illumination beam 125b guided to the object plane 170, which is specularly reflected without being scattered or diffracted by the object plane 170 (i.e., specular reflection components; components 185d that pass through a position away from the optical axis on the installation plane of the aperture filter 180d in the imaging optics 165), reaches the image sensor 193 plane of the camera 195 without being shielded by the light-shielding portion around the center of the aperture filter 180d, and thus contributes to the image formation.

Part of the components of the illumination beam 125b guided to the object plane 170, which are scattered or diffracted by the object plane 170 (i.e., components 185b, which passes through a position away from the optical axis on the installation plane of the aperture filter 180d in the imaging optics 165), reaches the images sensor 193 plane of the camera 195 through the annular aperture portion of the aperture filter 180d, and thus contributes to the image formation.

The former components correspond to bright-field light components, and the latter components correspond to dark-field light components. Thus, in this example, an image captured with the camera 195 is an image obtained by adding the bright-field image components that are entirely bright to the dark-field image with an enhanced edge.

It should be noted that FIG. 2B shows an example in which four support members that support the light-shielding portion provided on the center side of the annular aperture are arranged in parallel with or at right angles to a pattern formed on the object plane 170. That is, an example in which four support members are formed in parallel with the x-axis and the y-axis is shown. When the support members are arranged in such a manner, it is possible to allow, when a sample whose main patterns include vertical and horizontal patterns (i.e., patterns that are parallel with the x-axis direction and the y-axis direction in FIG. 1), such as a semiconductor wafer, is to be observed, observation of an excellent image without distortions while maintaining the isotropy of the way in which the image looks.

In contrast, as shown in FIG. 3, even when an aperture filter whose four support member positions are rotated by 45 degrees with respect to the optical axis is used as the aperture filter 180d of the imaging optics 165, it is also possible to obtain equivalent effects to those obtained when an aperture filter with the structure shown in FIG. 2B is used.

It should be noted that with regard to aperture filters for bright/dark field objective lenses that are used for the conventional optical microscopes, a light-shielding portion provided on the center side of an annular aperture is often supported from three directions. However, when the isotropy of the way in which an image looks is not a concern, it is also possible to adopt the structure in which the light-shielding portion provided on the center side of the annular aperture is supported from three directions, even for the aperture filter in this embodiment.

[Structure of Beam Splitter]

Figure 4A:
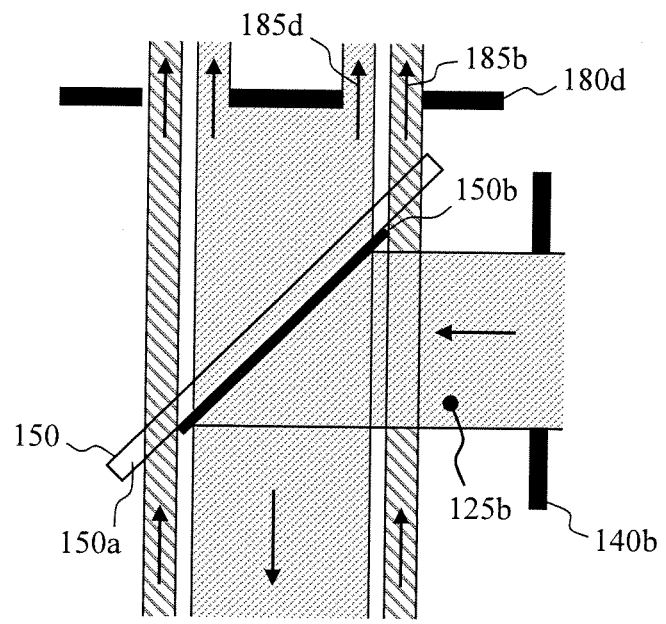
FIG. 4A shows an exemplary structure of a beam splitter of an optical microscope device.
Figure 4B:
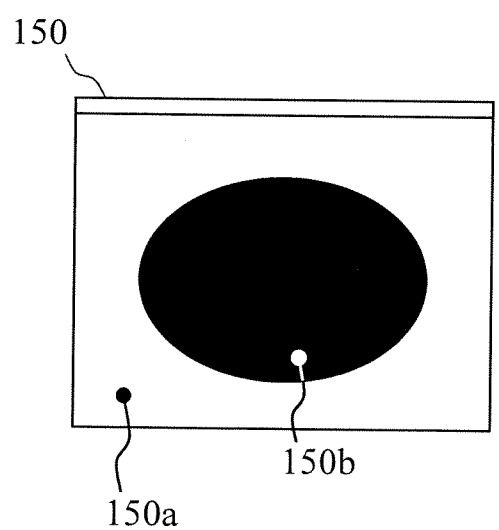
FIG. 4B shows an exemplary structure of a beam splitter of an optical microscope device.

FIGS. 4A and 4B show another exemplary structure of the beam splitter 150. The planar region of the beam splitter 150 includes a transmissive region 150a and a reflective region 150b. In this embodiment, the beam splitter 150 is formed of a transmissive substrate, and a film that reflects 50% or more of light is formed on the surface of the substrate corresponding to the reflective region 150b. Since the transmissive region 150a is formed of a transmissive substrate, it transmits light.

When the beam splitter 150 with such a structure is used, the transmittance of the light beam 185b reflected by the object plane 170 can be increased. In such a case, the brightness of the image 199 can be increased.

However, as shown in FIG. 4A, it is necessary to provide the illumination optics 120 with the aperture filter 140b, and set the light-shielding region of the aperture filter 140b so as to prevent the boundary plane between the reflective region 150b and the transmissive region 150a of the beam splitter 150 from being illuminated with an illumination beam. This is because, when such setting is not provided, an illumination beam scattered by the boundary plane between the reflective region 150b and the transmissive region 150a of the beam splitter 150 will become incident on the image sensor 193 via the imaging lens 190, which can lower the contrast of the image 199.

When it is necessary to change the illumination characteristics in accordance with the characteristics of a sample, it is also necessary to replace (switch) the beam splitter 150. Needless to say, replacement (switching) of the beam splitter 150 is difficult as it requires a switching mechanism with significantly higher precision than a case where the aperture filter 140b of the illumination optics 120 is merely switched or when the aperture size of a variable aperture filter is changed.

It should be noted that the reflectivity of the reflective region 150b of the beam splitter 150 is desirably optimized in accordance with the intended use. In order to increase the illumination efficiency, the reflectivity may be set to around 100%. However, when the reflectivity is 100%, some of components 185d of the components that are specularly reflected without being scattered and/or diffracted by the object plane 170 (i.e., specular reflection components; components 185d at a position away from the optical axis on the installation plane of the aperture filter 180d of the imaging optics) are reflected by the beam splitter 150, and thus does not contributes to the image formation.

When contribution of the specular reflection components to the image formation is necessary, it is preferable to set the reflectivity of the reflective region 150b of the beam splitter 150 to a low value between 50% and 100%. The reflectivity may be set so that the balance between the brightness of the image and the way in which the image looks can be optimal for recognizing a pattern on the sample plane.

[Device Configuration 2]

Figure 5:
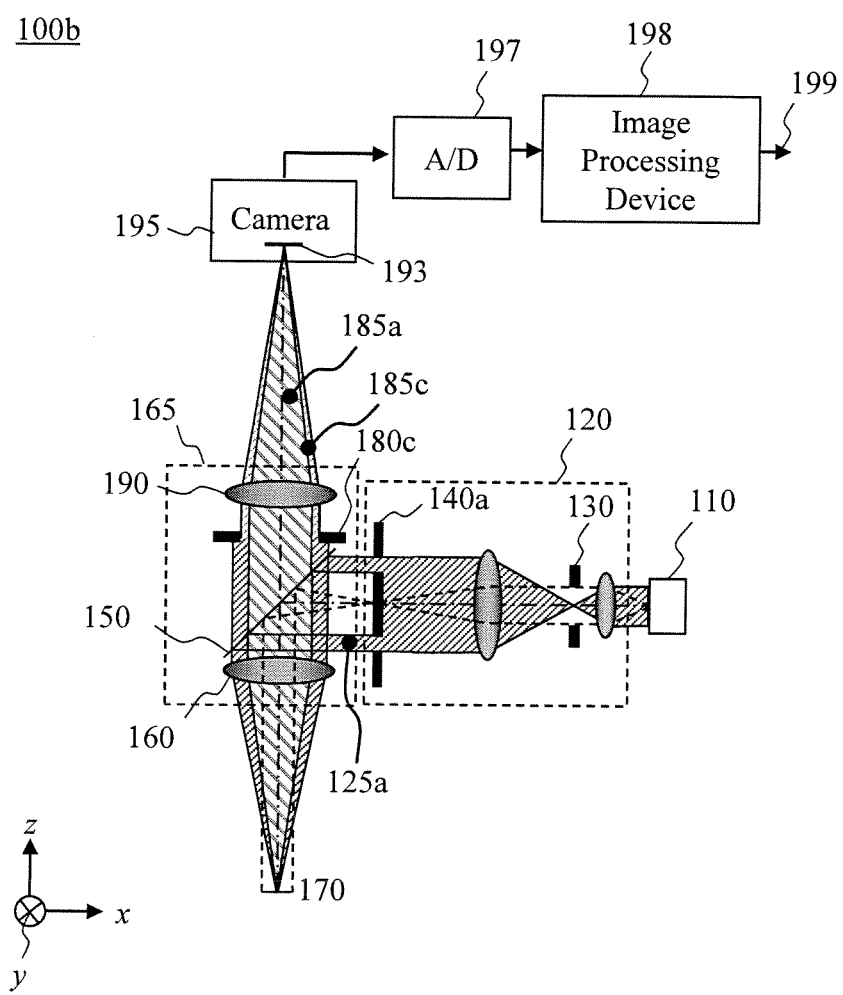
FIG. 5 shows another schematic configuration of an optical microscope device.

FIG. 5 shows the schematic configuration of an optical microscope device 100b in accordance with an embodiment. In FIG. 5, portions corresponding to those in FIG. 1 are represented by identical reference numerals. The difference between FIG. 5 and FIG. 1 lies in the characteristics of an aperture filter 140a of the illumination optics 120 and an aperture filter 180c of the imaging optics 165.

In this embodiment, an annular aperture with the structure shown in FIG. 2B or 3 is used as the aperture filter 140a of the illumination optics. In addition, the circular aperture shown in FIG. 2A is used as the aperture filter 180c of the imaging optics.

Further, the diameter d2 of the light-shielding portion at the center of the aperture filter 140a of the illumination optics and the diameter d3 of the circular aperture of the aperture filter 180c of the imaging optics satisfy a relationship of d3>d2. At this time, part of the components of an annular illumination beam 125a emerging from the illumination optics 120, which is specularly reflected without being scattered and/or diffracted by the object plane 170 (i.e., the sample) (i.e., specular reflection components; components 185c that pass through a position close to the optical axis on the installation plane of the aperture filter 180c of the imaging optics 165), reaches the image sensor 193 of the camera 195 without being shielded by the aperture filter 180c, and thus contributes to the image formation.

Meanwhile, components 185a of the components scattered and/or diffracted by the object plane 170 (i.e., the sample), which pass through a position close to the optical axis on the installation plane of the aperture filter 180c of the imaging optics, reach the image sensor 193 of the camera 195 through the aperture portion of aperture filter 180c of the imaging optics, and thus contributes to the image formation.

The former components correspond to bright-field light components, and the latter components correspond to dark-field light components. Thus, in this case, an image captured with the camera 195 is an image obtained by adding the bright-field image components that are entirely bright to the dark-field image with an enhanced edge.

It should be noted that annular illumination such as the one shown in this embodiment can also be realized without using the aperture filter 140a in the illumination optics. For example, it is also possible to form a film whose peripheral region that is away from the optical axis reflects light, and whose central portion around the optical axis transmits light, on the surface of a transparent substrate that forms the beam splitter 150.

However, in such a case, an illumination beam that is scattered by the boundary plane between the reflective region and the transmissive region of the beam splitter 150 becomes incident on the image sensor 193 via the imaging lens 190. Therefore, it would be impossible to avoid a decrease in contrast of the image 199.

Thus, as shown in FIG. 5, annular illumination is realized by using an element, which is obtained by forming a thin film with an approximately uniform transmittance distribution on the surface of a substrate, for the beam splitter 150, in combination with the aperture filter 140a of the illumination optics. Such a combined structure can acquire a sharp, high-contrast image.

Figure 6A:
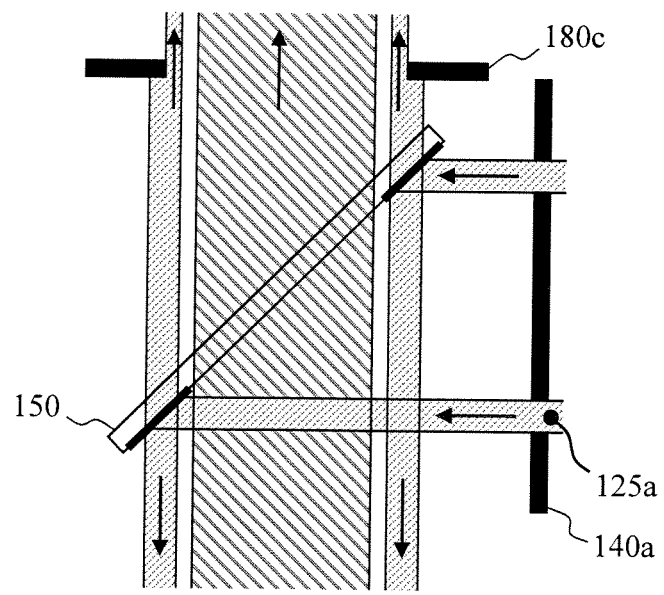
FIG. 6A shows an exemplary structure of a beam splitter of an optical microscope device.
Figure 6B:
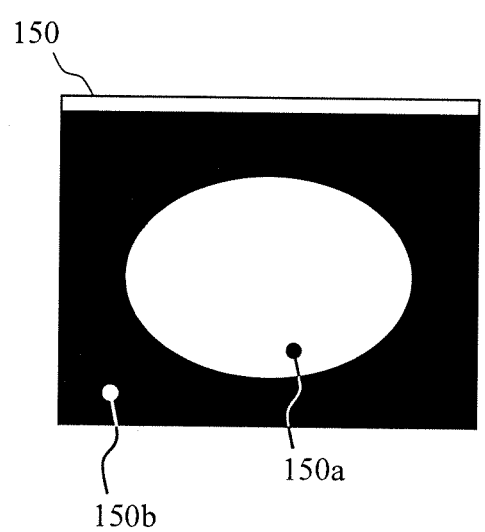
FIG. 6B shows an exemplary structure of a beam splitter of an optical microscope device.

It is also possible to, in addition to providing the aperture filter 140a of the illumination optics, use the beam splitter 150 with a structure shown in FIGS. 6A and 6B. The circumferential black region of the beam splitter 150 shown in FIGS. 6A and 6B is a light reflective region 150b, and the central portion is a transmissive region 150a that transmits light. Specifically, a reflective film with a shape corresponding to the reflective region 150b may be formed on the surface of the beam splitter 150.

A light-shielding region of the aperture filter 140a on the illumination optics 120 side is set to prevent the boundary portion between the reflective region 150b (with a reflectivity of 50% or greater) and the transmissive region 150a of the beam splitter 150 from being illuminated with an illumination beam. Accordingly, it is possible to obtain a high-contrast image while avoiding the aforementioned influence of scattered rays.

In this embodiment, it is possible to, in addition to obtaining the aforementioned effects, increase the transmittance of the beam splitter 150 with respect to the light components reflected by the sample plane. Therefore, a brighter image can be obtained in this embodiment. The reflectivity of the reflective region 150b of the beam splitter 150 is desirably optimized in accordance with the intended use as described above.

[Device Configuration 3]

Figure 7:
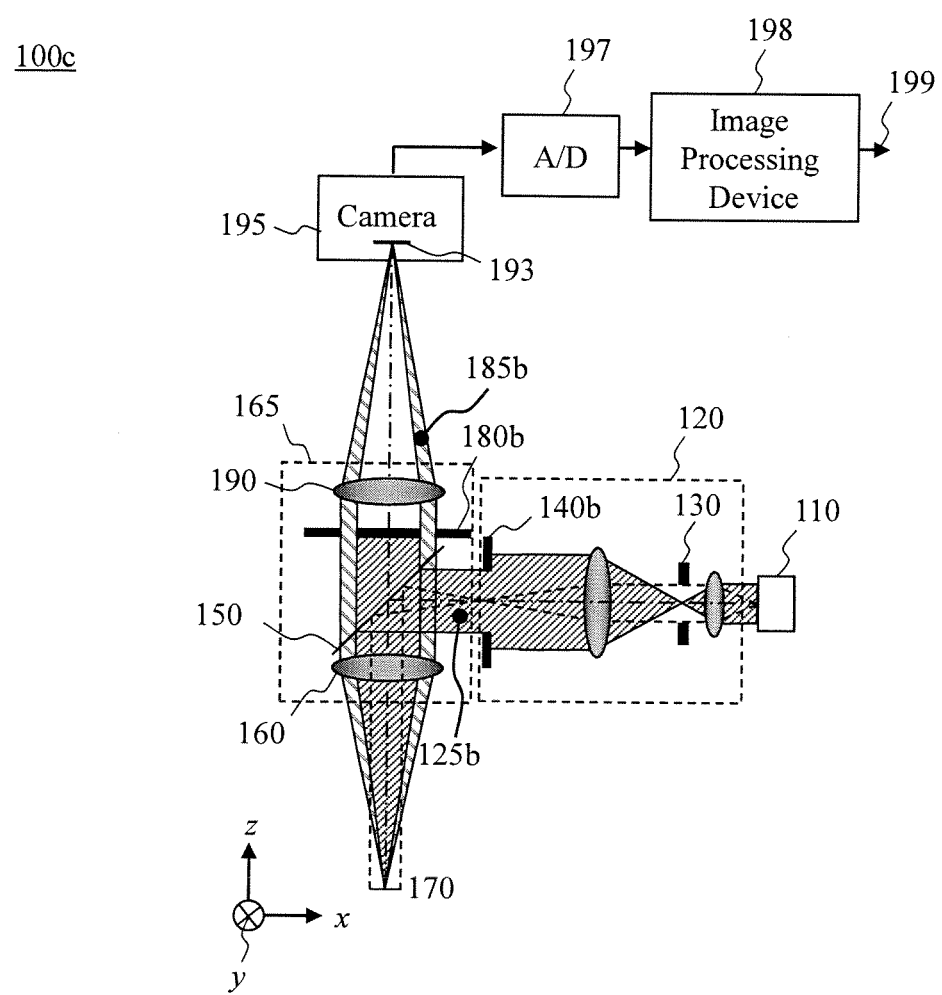
FIG. 7 shows another schematic configuration of an optical microscope device.

FIG. 7 shows the schematic configuration of an optical microscope device 100c in accordance with this embodiment. In FIG. 7, portions corresponding to those in FIG. 1 are represented by identical reference numerals. The difference between FIG. 7 and FIG. 1 lies in the characteristics of the aperture filter 140b of the illumination optics 120 and an aperture filter 180b of the imaging optics 165.

In this embodiment, an aperture filter with the circular aperture shown in FIG. 2A is used as the aperture filter 140b of the illumination optics 120 as in the embodiment shown in FIG. 1. Meanwhile, an aperture filter with the annular aperture shown in FIG. 2B or 3 is used as the aperture filter 180b of the imaging optics 165.

It should be noted that the diameter d3 of the circular aperture of the aperture filter 140b of the illumination optics and the diameter d2 of the shielding portion located at the center of the aperture filter 180b of the imaging optics satisfy a relationship of d3≤d2. At this time, part of the components of an illumination beam 125b emerging from the illumination optics 120, which is specularly reflected without being scattered and/or diffracted by the sample, is completely shielded by the aperture filter 180b of the imaging optics, and thus does not contribute to the image formation. Meanwhile, components 185b of the components scattered and/or diffracted by the sample, which pass through a position away from the optical axis on the plane of the aperture filter 180b of the imaging optics, reach the image sensor 193 of the camera 195 through the annular aperture portion of the aperture filter 180b of the imaging optics, and thus contributes to the image formation.

In this embodiment, the components of light corresponding to the bright-field light components do not contribute to the image formation, and only the dark-field light components contribute to the image formation. Thus, in this embodiment, an image captured with the camera 195 is a dark-field image with an enhanced edge.

It should be noted that as shown in FIGS. 1 and 7, when the aperture filter of the imaging optics has an annular aperture, the coefficient of MTF in a low spatial frequency region becomes lower than MTF at the diffraction limit. Consequently, there may be cases where the sharpness of the captured image becomes low. When the sharpness is low, an inverse filter may be applied to the captured image in the image processing device 198 to enhance the spatial frequency components with the decreased contrast.

When MTF is lowered due to the aperture filter, there is no spatial frequency at which the coefficient of MTF becomes zero, unlike blurring that would occur due to out-of-focus blur. Thus, there are no cases where noise becomes dominant due to the presence of the inverse filter, and thus, the sharpness of the image can be recovered.

[Device Configuration 4]

Figure 8:
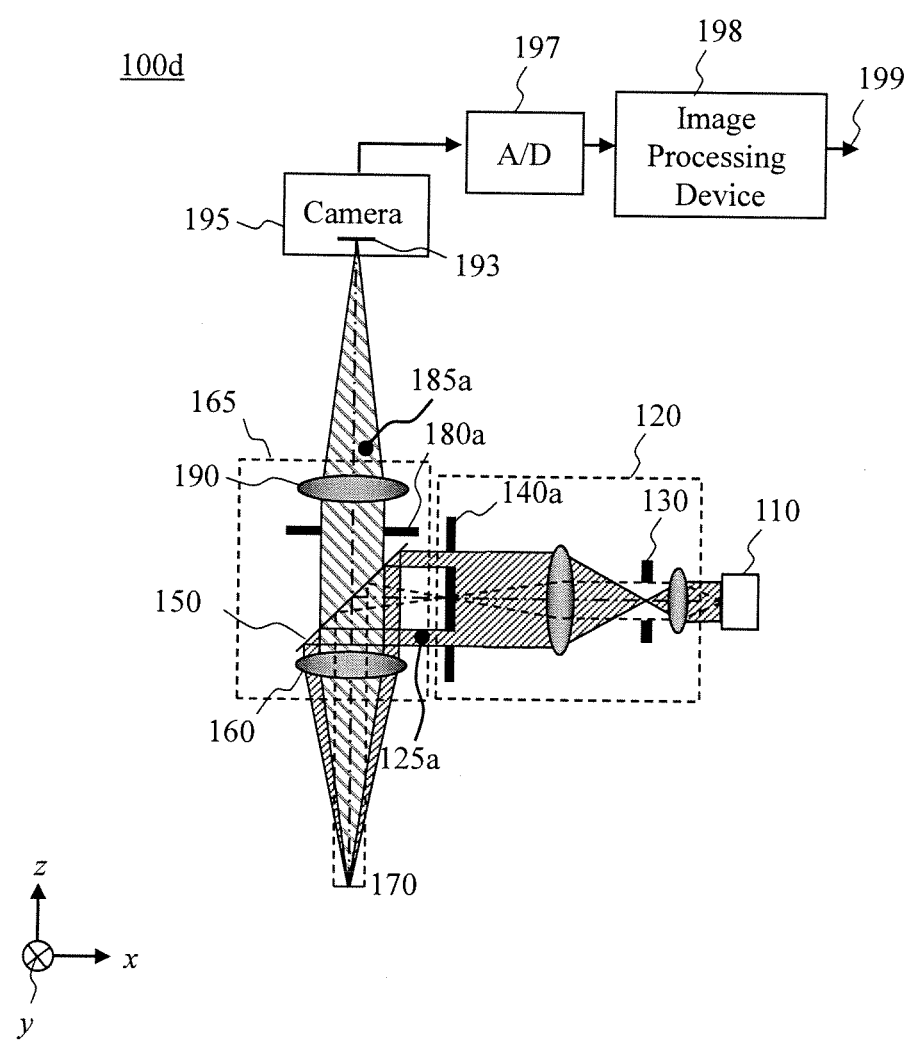
FIG. 8 shows another schematic configuration of an optical microscope device.

FIG. 8 shows another schematic configuration of an optical microscope device 100d in accordance with an embodiment. In FIG. 8, portions corresponding to those in FIG. 1 are represented by identical reference numerals. The difference between FIG. 8 and FIG. 1 lies in the characteristics of the aperture filter 140a of the illumination optics 120 and the aperture filter 180a of the imaging optics.

In this embodiment, an aperture filter with the annular aperture shown in FIG. 2B or 3 is used as the aperture filter 140a of the illumination optics. Meanwhile, an aperture filter with the circular aperture shown in FIG. 2A is used as the aperture filter 180a of the imaging optics.

Further, the diameter d2 of the light shielding portion located at the center of the aperture filter 140a of the illumination optics and the diameter d3 of the circular aperture of the aperture filter 180*a* of the imaging optics satisfy a relationship of d3≤d2. At this time, part of the components of an annular illumination beam 125*a* emerging from the illumination optics 120, which is specularly reflected without being scattered and/or diffracted by the sample (i.e., specular reflection components), is completely shielded by the aperture filter 180*a* of the imaging optics, and thus does not contribute to the image formation. Meanwhile, components 185*a* of the components scattered and/or diffracted by the sample, which pass through a position close to the optical axis on the plane of the aperture filter 180*a* of the imaging optics, reach the image sensor 193 of the camera 195 through the aperture portion of the aperture filter 180*a* of the imaging optics, and thus contributes to the image formation.

In this embodiment, the components of light corresponding to the bright-field light components do not contribute to the image formation, and only the dark-field light components contribute to the image formation. Thus, in this embodiment, an image captured with the camera 195 is a dark-field image with an enhanced edge.

[Device Configuration 5]

Figure 9:
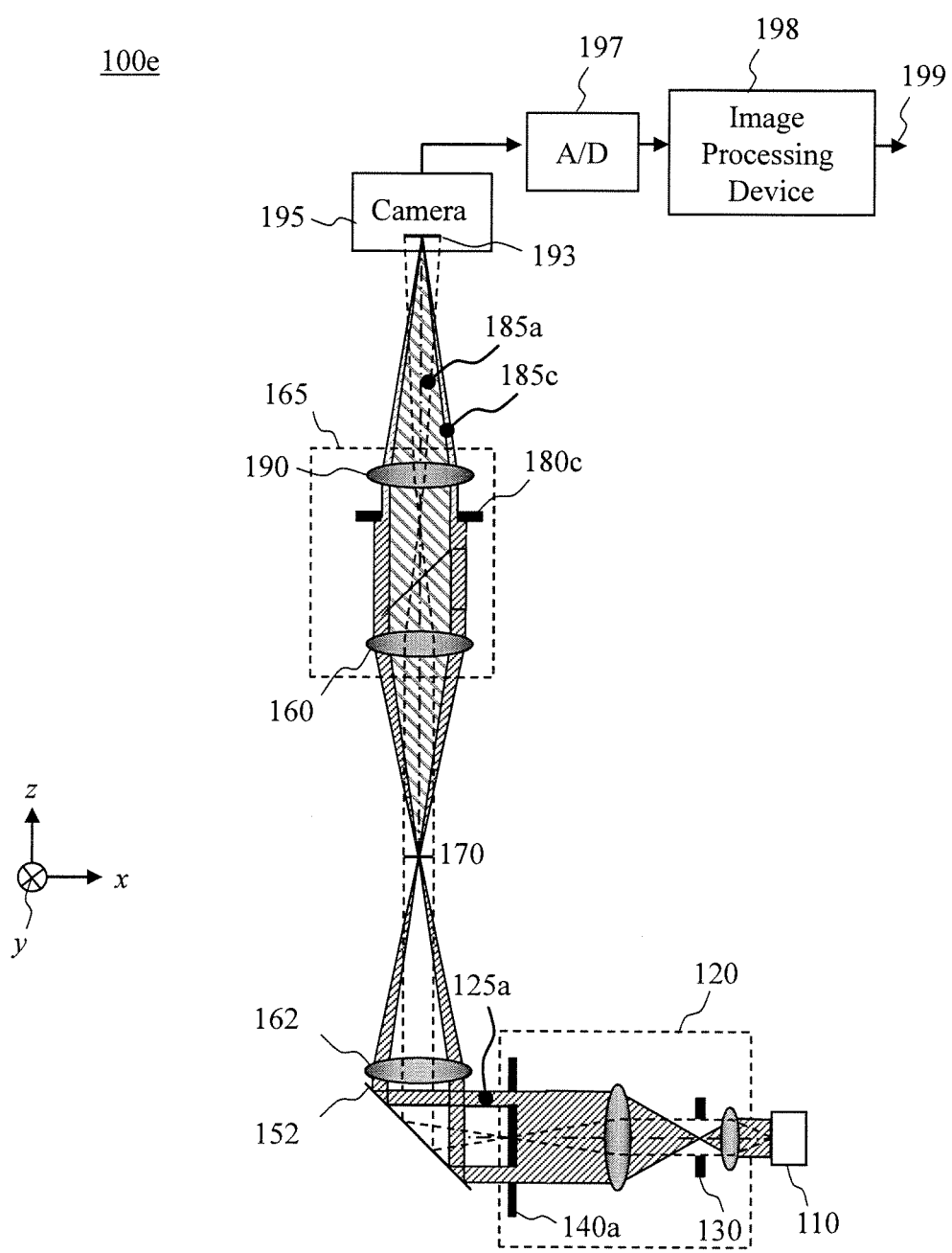
FIG. 9 shows the schematic configuration of an optical microscope device for observing a sample that transmits light.

FIG. 9 shows the schematic configuration of an optical microscope device 100*e* in accordance with an embodiment. In FIG. 9, portions corresponding to those in FIG. 1 are represented by identical reference numerals. The optical microscope device 100*e* in accordance with this embodiment is characterized in adopting transmissive illumination optics to observe a transmissive object. For example, the optical microscope device 100*e* is suitably applied to observation or inspection of a glass substrate or the like.

In this embodiment, an aperture filter with the annular aperture shown in FIG. 2B or 3 is used as the aperture filter 140*a* of the illumination optics. Meanwhile, an aperture filter with the circular aperture shown in FIG. 2A is used as the aperture filter 180*c* of the imaging optics.

Further, the diameter d2 of the light-shielding portion located at the center of the aperture filter 140*a* of the illumination optics and the diameter d3 of the circular aperture of the aperture filter 180*c* of the imaging optics satisfy a relationship of d3>d2. At this time, part of an annular illumination beam 125*a* emerging from the illumination optics 120, which is transmitted without being scattered and/or diffracted by the sample (i.e., transmitted light components; components 185*c* that pass through a side close to the optical axis on the plane of the aperture filter 180*c* of the imaging optics), reaches the image sensor 193 of the camera 195 without being shielded by the aperture filter 180*c* of the imaging optics, and thus contributes to the image formation.

Components 185*a* of the components scattered and/or diffracted by the sample, which pass through a position around the optical axis on the plane of the aperture filter 180*c* of the imaging optics, reach the image sensor 193 of the camera 195 through the aperture portion of the aperture filter 180*c* of the imaging optics, and thus contributes to the image formation.

The former components correspond to bright-field light components, and the latter components correspond to dark-field light components. Thus, in this embodiment, an image captured with the camera 195 is an image obtained by adding the bright-field image components that are entirely bright to the dark-field image with an enhanced edge, in accordance with a similar principle to that in FIG. 1.

[Effects of Imaging Capturing of Each Device]

Figure 10A:
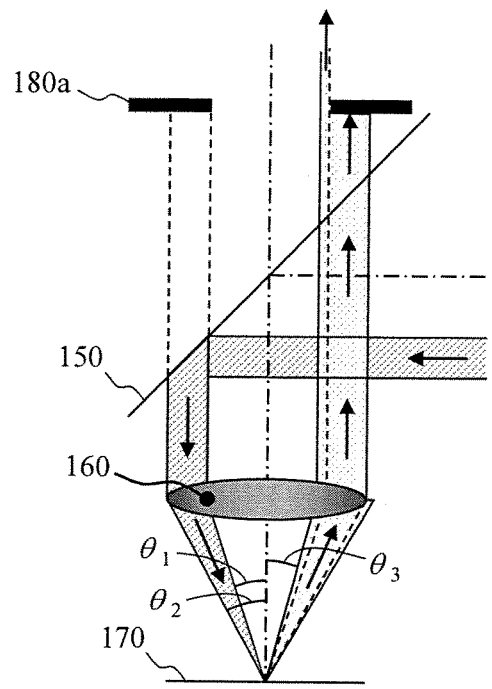
FIG. 10A illustrates an illumination effect obtained by a combination of an illumination beam and optics.

Effects of the image capturing method in accordance with each embodiment will be described with reference to FIGS. 10A and 10B. FIG. 10A shows the optical path of an illumination beam and the optical path of a reflected beam on the sample surface when dark-field observation is conducted by illuminating the sample through annular illumination.

In practice, an illumination beam that is allowed to be incident on the sample overlaps a light beam that is reflected by the sample in response to another illumination beam that has been allowed to be incident on the sample from a position opposite the former illumination beam with the optical axis interposed therebetween. However, in FIGS. 10A and 10B, the optical path of the other illumination beam in the opposite relationship is omitted to clearly show a spread of the reflected beam due to scattering.

The angle $\theta_1$ shown in the drawings represents the angle corresponding to NA on the object side of the imaging optics, and also represents the minimum value of the incident angle of the illumination beam. Meanwhile, the angle $\theta_2$ represents the maximum value of the incident angle of the illumination beam. The angle $\theta_3$ represents the minimum value of the angle of the reflected beam with respect to the normal line of the sample plane.

When the sample plane has a pattern formed thereon, the reflected beam will spread due to the influence of diffraction and/or scattering, and $\theta_3$ becomes smaller than $\theta_1$. In such a case, part of the reflected beam (components at angles between the angle $\theta_3$ and the angle $\theta_1$) passes through the aperture of the aperture filter 180*a* of the imaging optics, and thus reaches the image sensor 193 of the camera 195 and is imaged as a bright point.

Figure 10B:
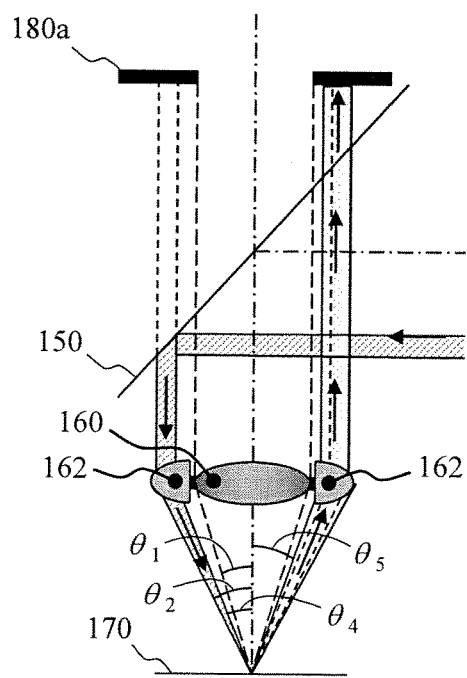
FIG. 10B illustrates an illumination effect obtained by a combination of an illumination beam and optics.

Meanwhile, FIG. 10B shows a case where a lens structure is adopted in which an optical element 162 for dark-field illumination is provided on the outer side of the imaging objective lens 160. In this case, the sample (i.e., the object plane 170) is illuminated with annular illumination that passes through the optical element 162 for dark-field illumination. In FIG. 10B, an illumination beam that is allowed to be incident from an opposite position with the optical axis interposed therebetween is also omitted to clearly show a spread of the reflected beam due to scattering as in FIG. 10A.

The angle $\theta_1$ shown in FIG. 10B represents the angle corresponding to NA on the object side of the imaging optics. The angle $\theta_2$ represents the maximum value of the incident angle of the illumination beam, and the angle $\theta_4$ represents the minimum value of the incident angle of the illumination beam. Meanwhile, the angle $\theta_5$ represents the minimum value of the angle of the reflected beam with respect to the normal line of the sample plane.

When the sample plane has a pattern formed thereon, the reflected beam will spread due to the influence of diffraction and scattering, and $\theta_5$ becomes smaller than $\theta_4$. When $\theta_5$ becomes smaller than $\theta_1$, in particular, part of the reflected beam reaches the image sensor 193 of the camera 195 through the aperture of the aperture filter 180*a* of the imaging optics, and is imaged as a bright point.

FIG. 10B differs from FIG. 10A in that an image is not formed when $\theta_5$ is between $\theta_4$ and $\theta_1$. When a difference in level of a pattern on the sample plane is extremely smaller than the wavelength, for example, less than or equal to 1/10 of the wavelength, a spread of scattered rays (i.e., the difference between $\theta_5$ and $\theta_4$) is small, and $\theta_5$ may fall within the range between $\theta_4$ and $\theta_1$. The holder of the objective lens 160 and the optical element 162 for dark-field illumination may be configured so as to reduce the difference between $\theta_4$ and $\theta_1$, but it cannot be set to zero due to the structural limit.

Thus, in the case of FIG. 10B, a pattern with a very small difference in level may not be able to be recognized as an image. In contrast, with the configuration shown in FIG. 10A (the method of each embodiment), the angle corresponding to the difference between $\theta_4$ and $\theta_1$ in FIG. 10B can be set to zero. Thus, such a configuration is suitable for recognizing a pattern with a very small difference in level as an image.

[Device Configuration 6]

Figure 11A:
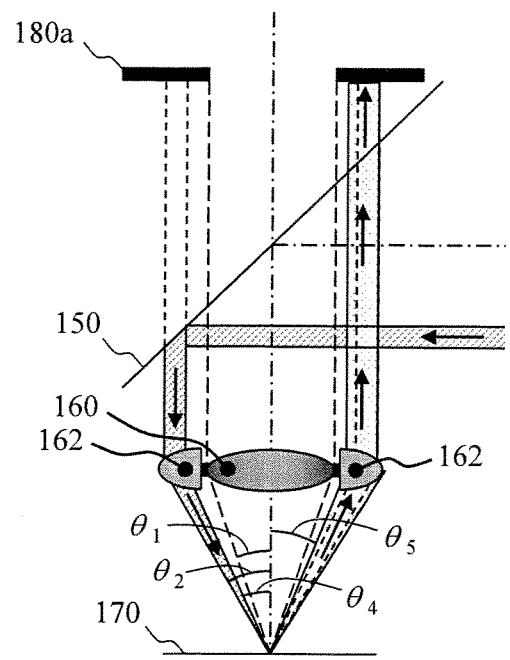
FIG. 11A illustrates an illumination effect obtained by a combination of an illumination beam and optics.
Figure 11B:
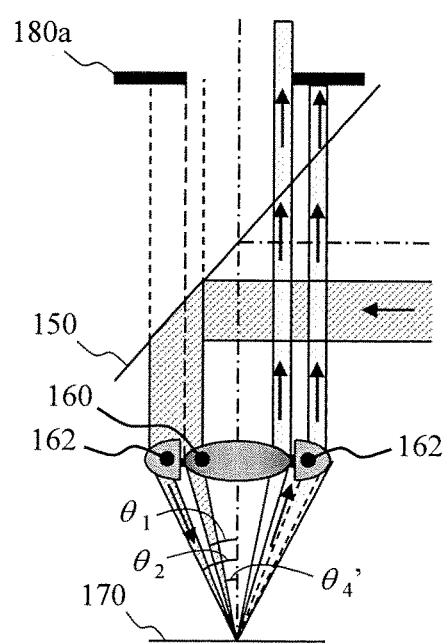
FIG. 11B illustrates an illumination effect obtained by a combination of an illumination beam and optics.

FIGS. 11A and 11B show exemplary configurations of other optics that are suitably used for the optical microscope device 100b shown in FIG. 5. Described herein is a method of implementing image capturing of the optical microscope device 100b, using the optical element 162 for dark-field illumination that is arranged on the outer side of the imaging objective lens 160.

FIG. 11A shows the setting performed in capturing an image in a totally dark field. To this end, a sample (i.e., the object plane 170) is irradiated with an illumination beam through the optical element 162 for dark-field illumination, and a direct reflected beam is completely shielded by the aperture filter 180a of the imaging optics.

FIG. 11B shows an embodiment of a method of capturing an image by combining bright-field light components with dark-field light components in the optical microscope device 100b shown in FIG. 5. In FIG. 11B, the width of an illumination beam that has been allowed to be incident annularly is widened in the inner side direction of the annular beam so that part of the illumination beam reaches the sample (i.e., the object plane 170) through the objective lens 160. Accordingly, it becomes possible to capture an image that is formed by both dark-field illumination components that have passed through the optical element 162 for dark-field illumination and bright-field illumination components that have passed through the objective lens 160.

[Applied Device]

Figure 12:
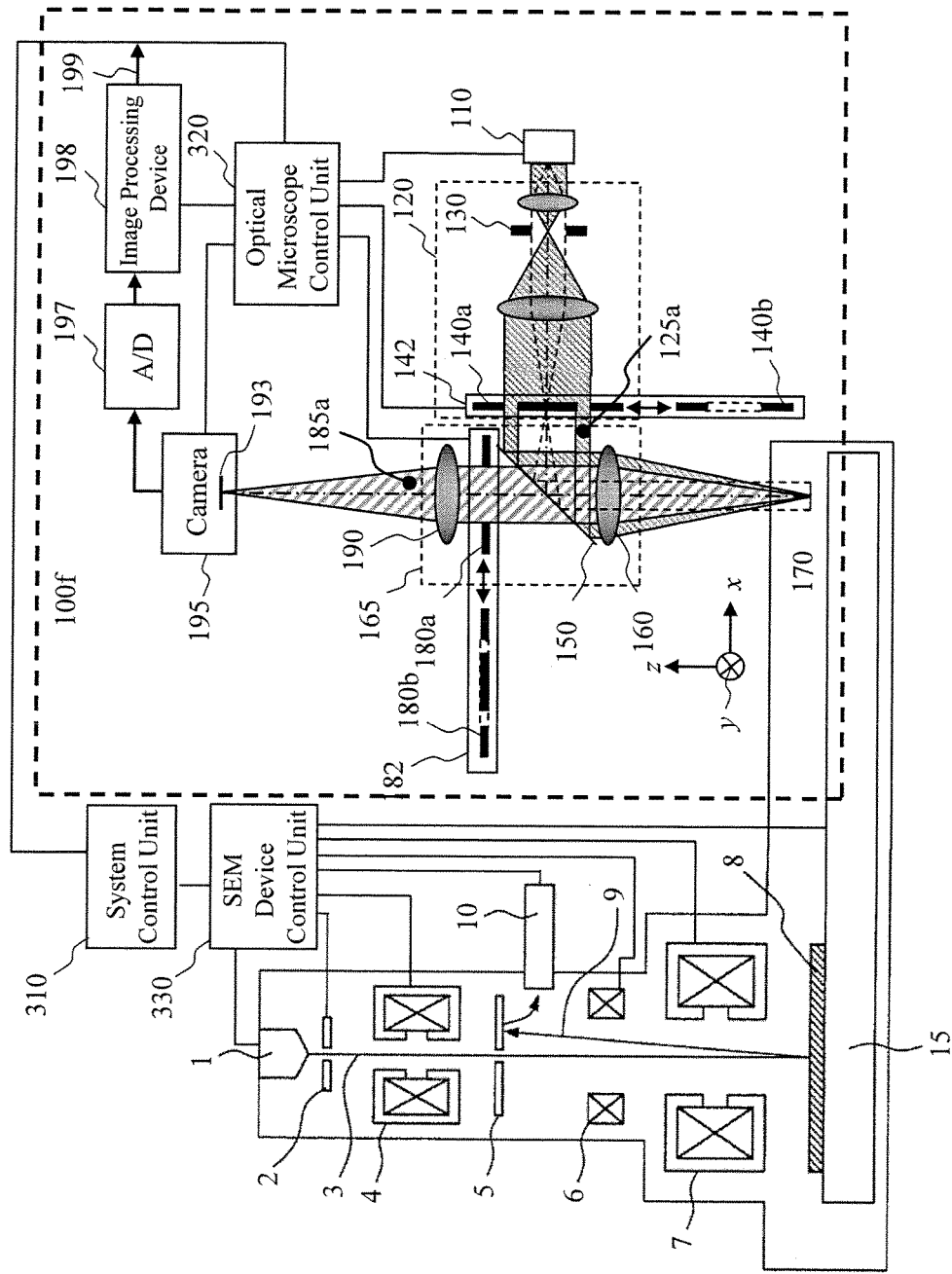
FIG. 12 shows the schematic configuration of an inspection apparatus having an optical microscope device.

FIG. 12 shows an exemplary configuration of the whole inspection apparatus to which the aforementioned device configuration is applied. The inspection apparatus shown in FIG. 12 includes a charged particle beam apparatus used to acquire an image for inspecting and an optical microscope device 100f used to align a sample at a predetermined position.

In this embodiment, a scanning electron microscope (SEM) device is used as the charged particle beam device. The SEM device is controlled by a SEM device control unit 330. Meanwhile, the optical microscope device 100f is controlled by an optical microscope control unit 320. The whole inspection apparatus is controlled by a system control unit 310 having a user interface.

In the SEM device, electrons generated from an electron source 1 are accelerated by a primary electron accelerating electrode 2, and are then guided to an objective lens 7 via a condenser lens 4. The electrons herein are focused by the objective lens 7, and are caused to irradiate a sample 8 as a primary electron beam. Secondary electrons 9 are generated from the position irradiated with the primary electron beam.

The secondary electrons 9 collide with a reflecting plate 5 to generate new secondary electrons. The secondary electrons generated by the reflecting plate 5 are captured by a secondary electron detector 10. The output of the secondary electron detector 10 changes in accordance with the amount of electrons that become incident on the secondary electron detector 10.

In the SEM device, an electron beam is deflected by a scanning coil 6 to scan the sample surface with the electron beam. In synchronism with the scanning, the output of the secondary electron detector 10 is converted into a gray level of an image and is recorded, whereby the shape of the sample surface can be acquired as a two-dimensional image. Using such an image can execute an inspection of the dimensions of a pattern on the sample, an inspection for pattern defects on the sample, and an inspection for foreign substances or the like on the sample.

For the optical microscope device 100f, any of the optical microscope devices shown in FIGS. 1, 5, 7, and 8 can be used. In this embodiment, the optical microscope device 100d shown in FIG. 8 is used. It should be noted that in this example, a planar element, which has formed thereon a thin film with an approximately uniform transmittance distribution, is used for the beam splitter 150. In addition, in this example, aperture filter switching mechanisms 142 and 182 are mounted on the aperture filter 140a of the illumination optics and the aperture filter 180a of the imaging optics, respectively.

The aperture filter switching mechanism 142 of the illumination optics switches between the aperture filter 140a with an annular aperture and the aperture filter 140b with a circular aperture. Meanwhile, the aperture filter switching mechanism 182 of the imaging optics switches between the aperture filter 180a with a circular aperture and the aperture filter 180b with an annular aperture.

Each of the aperture filters of the illumination optics and the aperture filters of the imaging optics is used as a transmissive aperture filter, and, a deviation of about 0.1 mm can be tolerated. Therefore, an inexpensive switching mechanism can be used.

With the aperture filter switching mechanisms 142 and 182 mounted, it is possible to selectively use the single optical microscope device 100f as the optical microscope device 100c shown in FIG. 7 or the optical microscope device 100d shown in FIG. 8. Alternatively, with the aperture filter switching mechanisms 142 and 182 mounted, it is possible to selectively use the single optical microscope device 100f as the optical microscope device 100a shown in FIG. 1 or the optical microscope device 100b shown in FIG. 5. That is, switching between the aperture filters allows implementation of two types of optical structures with the use of the single optical microscope device 100f.

Further, when iris diaphragms are applied as the individual aperture filters to allow the aperture sizes of the aperture filters to be variable, it is possible to implement the four types of optics shown in FIGS. 1, 5, 7, and 8 with the use of a single optical microscope device.

It is also possible to adopt the beam splitters 150 each having the reflective region 150b and the transmissive region 150a as shown in FIGS. 4A, 4B, 6A, and 6B and allow switching between one of the plurality of beam splitters 150, though it will increase cost. When a switching mechanism is mounted, utilization efficiency of an illumination beam can be optimized. Thus, a brighter image can be obtained using a light source with low power consumption.

[Sample Observation]

Figure 13:
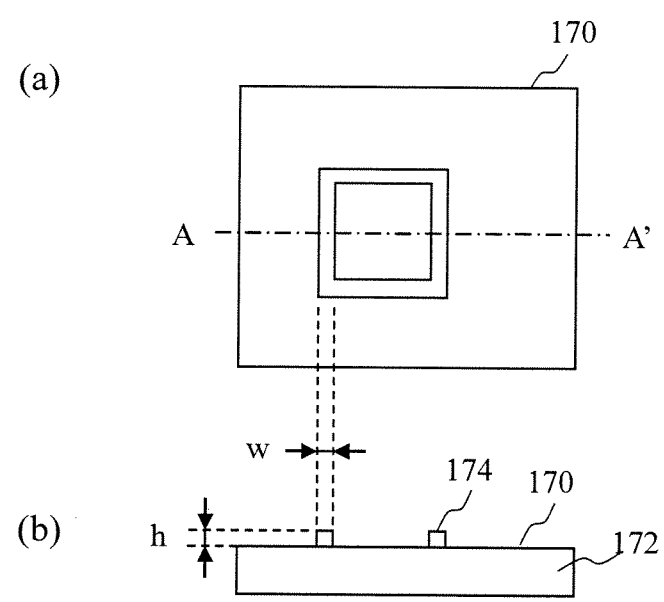
FIG. 13 shows an exemplary structure of a sample observed with an optical microscope device.

FIG. 13 shows an example of a sample for which only low contrast can be obtained in bright-field observation. FIG. 13(a) shows a plan view of the sample 170, and FIG. 13(b) shows a cross-sectional view of the sample 170 along A-A'. The sample 170 includes a substrate 172 and a pattern 174. In the case of a semiconductor wafer, the pattern 174 is often formed by straight lines. Needless to say, an isolated pattern can have a curved pattern 174. FIG. 13 shows a rectangular pattern formed by straight lines with a line width of W and a pattern height (i.e., a difference in level) of h.

The material of the pattern 174 may be the same as the material of the substrate 172 like an etched pattern on a Si substrate, or a material that transmits light like a resist. In the former case, when the height h of the pattern 174 is smaller than the wavelength of a light beam to be observed or imaged, contrast in bright-field observation is low, and thus, the pattern is difficult to discriminate. Meanwhile, in the latter case, even when the height h of the pattern 174 is relatively large, contrast in bright-field observation is low, and thus, the pattern is difficult to discriminate. This is because there is no difference in light reflectivity between the background portion and the pattern portion in both cases.

Figure 14:
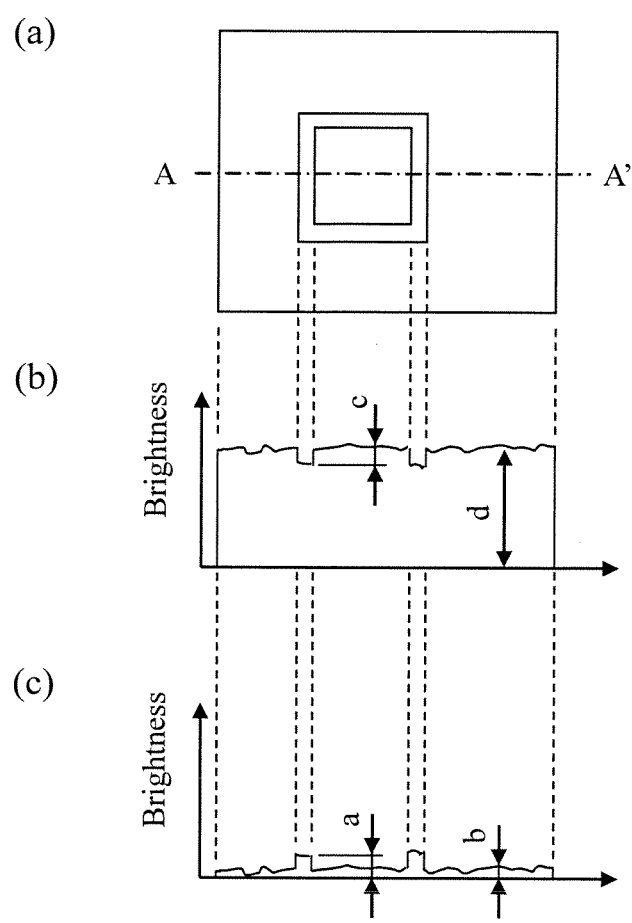
FIG. 14 shows an exemplary signal of an image captured with an optical microscope device.

FIG. 14 shows the feature of the observed image of the pattern 174 shown in FIG. 13. It should be noted that FIG. 14(a) shows an optical image of the sample, and FIGS. 14(b) and 14(c) each show a brightness profile of the optical image of the sample along line A-A'. The profile shown in FIG. 14(b) is an exemplary profile of a bright-field observation image. The profile shown in FIG. 14(c) is an exemplary profile of a dark-field observation image.

As described previously, an optical image of a sample, which has no difference in light reflectivity between the background portion and the pattern portion, obtained in bright-field observation is an entirely bright image as shown in the profile of FIG. 14(b). It should be noted that in the pattern portion, the amount of light that contributes to the image formation slightly decreases due to light scattering. Therefore, the pattern looks dark in many cases.

Provided that the brightness of the background portion is "d" and the decreased amount of the brightness of the pattern portion is "c," the optical contrast C_BF can be represented by:

$$C\_BF \cong c/(2d)$$

Thus, a sample that has no difference in light reflectivity between the background portion and the pattern portion has low optical contrast C_BF.

Meanwhile, an optical image obtained in dark-field observation is an entirely dark image as shown in the profile of FIG. 14(c). As shown in FIG. 7 or 8, for a portion having no pattern, specular reflection components of an illumination beam are totally shielded by the imaging optics. Therefore, an optical image obtained by the image sensor 193 is dark. Meanwhile, for a pattern portion, a slight amount of light is caused to pass through the imaging optics due to light scattering, thereby contributing to an image. Therefore, the pattern looks bright. Provided that the brightness of the background portion is b and the brightness of the pattern portion is a, the optical contrast C_DF can be represented by:

$$C\_DF = (a-b)/(a+b)$$

Therefore, if light scattered by the pattern portion can be captured in large quantities by the imaging optics, contrast can be increased.

As described above, dark-field observation is suitable for observation of a pattern that has low contrast in bright-field observation.

Figure 15:
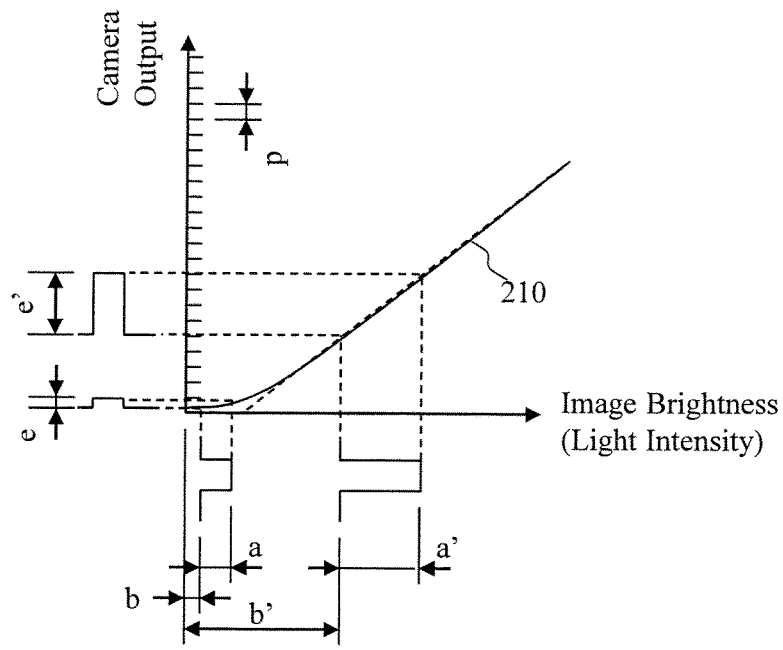
FIG. 15 shows an exemplary sensor output of an optical microscope device.

However, in dark-field observation, a shortage of brightness becomes a problem in capturing an optical image with the camera 195. FIG. 15 shows the relationship between the brightness of an optical image formed on the image plane of the image sensor 193 and an analog signal output from the camera 195. The abscissa axis indicates the brightness of the optical image, and the ordinate axis indicates the analog output signal level of the camera 195. In addition, a curve 210 represents the photoelectric conversion characteristics of the camera 195.

The analog output signal of the camera 195 is converted into a digital signal by the A/D converter 197. The scale of the width p shown on the ordinate axis of FIG. 15 indicates the step width in A/D conversion. As shown by the curve 210, the photoelectric conversion characteristics of the camera 195 are linear in regions of high light intensity, but are not linear in regions of low light intensity in many cases. Meanwhile, an optical image obtained in dark-field observation has a dark background but also has low light intensity in the pattern portion in many cases.

When the profile shown in FIG. 14(c) (the brightness of the background is represented by b and the brightness of the pattern portion is represented by a) is represented on the abscissa axis of FIG. 15, both the brightnesses a and b fall within the nonlinear region. In this case, the amplitude of the analog output signal of the camera 195 has a level of e at maximum, and becomes zero when subjected to A/D conversion. That is, the pattern cannot be recognized on the output image 199.

As solutions to this, a method of using an illumination light source with a higher output level for the illumination light source 110, a method of increasing the illumination efficiency of the illumination optics 120, and the like are considered. If the amount of light for irradiating the sample can be increased, it is possible to increase the brightness of the background to b' and the brightness of the pattern portion to a' as shown in FIG. 15. In such a case, the maximum amplitude level of the analog output signal corresponding to the pattern portion becomes e' that is at a detectable level even after subjected to A/D conversion.

However, a light source with a high output level is problematic in that it has a large volume, is costly, and needs a long development time. In addition, the illumination efficiency has a theoretical limitation, and has little room for improvement.

Figure 16:
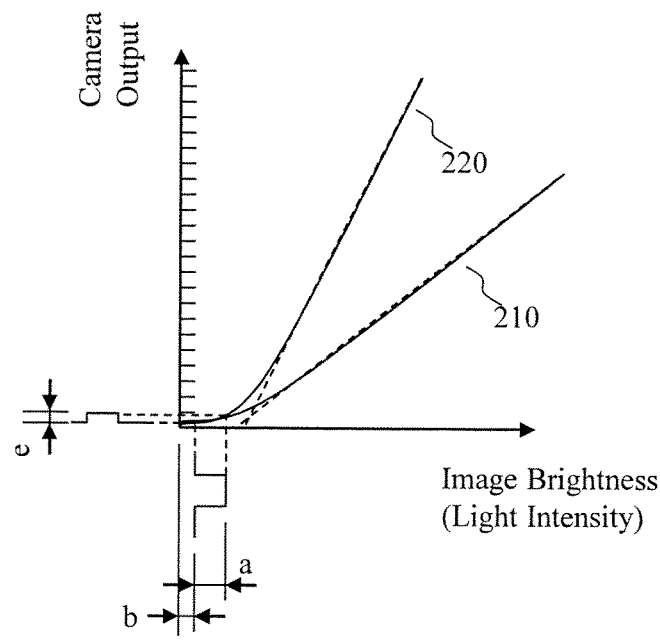
FIG. 16 shows an exemplary sensor output of an optical microscope device.

Meanwhile, increasing the photoelectric conversion gain of the camera 195 is also considered as another measure. FIG. 16 shows the principle diagram for this case. A curve 220 represents the photoelectric conversion characteristics of the camera 195 with an increased gain. As shown, increasing the gain can increase the output signal level with respect to the light intensity in a region where the light intensity is greater than or equal to a given level. However, in a region where the light intensity is originally low like the brightnesses a and b shown in FIG. 16, the analog output signal level does not change almost at all, and thus, the effect of increasing the gain of the camera 195 cannot be obtained.

In contrast, when the optical microscope device shown in FIG. 1 or 5 is used, it is possible to increase the background brightness of an optical image to a level detectable with the camera 195 by adding specular reflection components to an optical image obtained in dark-field observation. The thus obtained optical image is captured with the camera 195 with a high photoelectric conversion gain.

Figure 17:
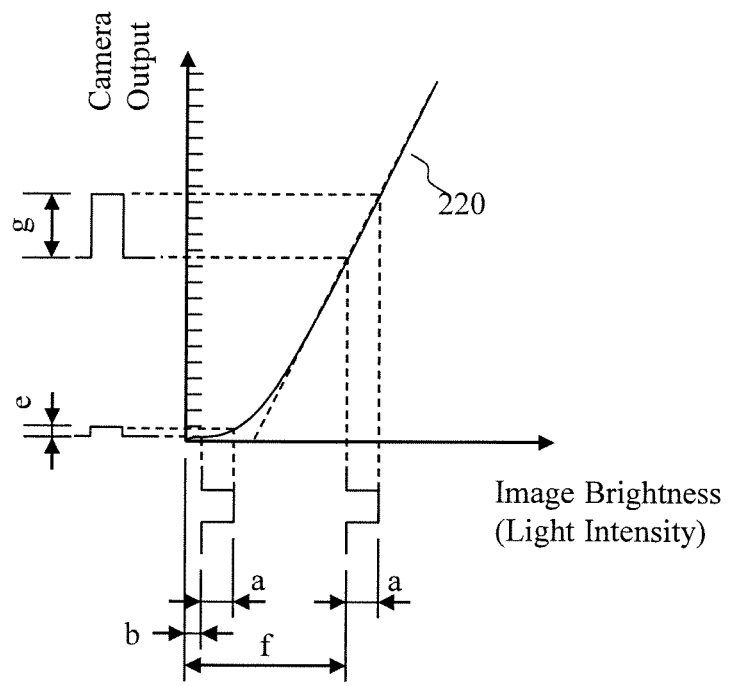
FIG. 17 shows an exemplary sensor output of an optical microscope device.

FIG. 17 shows the waveform of an analog output signal output from the camera 195 when the optical microscope device shown in FIG. 1 or 5 is used. First, as can be seen from the abscissa axis, the background brightness of an image is increased from b to f when specular reflection components are added to an optical image of dark-field light components. When an image of the light components is captured with the camera 195 with a high photoelectric conversion gain, it is possible to increase the analog output signal level for a pattern portion, for which only a level of e has been able to be originally obtained, to g. Consequently, when the method of the aforementioned embodiment is used, it is possible to obtain an analog output signal that can be detected even after subjected to A/D conversion, without using the illumination light source 110 with a high output level.

[Conclusion]

As described above, when the device configuration in accordance with each embodiment is adopted, it is possible to obtain sufficient contrast for even a sample for which sufficient contrast has not been able to be obtained in the conventional bright-field observation. Further, when each microscope device is applied to an inspection apparatus for semiconductor wafers, it is possible to stably obtain pattern contrast that is necessary for wafer alignment.

[Another Exemplary Device]

Although the aforementioned embodiments illustrate examples in which an illumination beam is guided to a sample (i.e., the object plane 170) through the objective lens 160 that partially constitutes the imaging optics 165, such a method may also be used in combination with a method of guiding an illumination beam to the sample from the outer side of the objective lens as used for the conventional bright/dark field objective lenses.

Although the aforementioned embodiments illustrate cases where the sample is basically a reflective object, it is also possible to apply such embodiments to a case where a transmissive object is observed through transmissive illumination as described with reference to Device Configuration 5.

The present invention is not limited to the aforementioned embodiments, and includes a variety of variations. For example, although the aforementioned embodiments have been described in detail to clearly illustrate the present invention, the present invention need not include all of the structures described in the embodiments. It is possible to replace a part of a structure of an embodiment with a structure of another embodiment. In addition, it is also possible to add, to a structure of an embodiment, a structure of another embodiment. Further, it is also possible to, for a part of a structure of each embodiment, add/remove/substitute a structure of another embodiment.

REFERENCE SIGNS LIST 100a, 100b, 100c, 100d, 100e, 100f: Optical microscope device
110: Illumination light source
120: Illumination optics
165: Imaging optics
180a, 180b, 180c, 180d: Aperture filter of imaging optics
193: Image sensor
140a, 140b: Aperture filter of illumination optics
170: Object plane (sample plane) of imaging optics

The invention claimed is:

1. An optical microscope device for observing or capturing a magnified image of a sample, the device comprising: an illumination light source; an illumination optics adapted to guide a light beam from the illumination light source to the sample; an imaging optics adapted to collect a light beam from the sample and form an image of the sample; a first aperture filter arranged on a system stop plane of the imaging optics, the first aperture filter being adapted to attenuate a specular reflection component; an image sensor arranged on an image plane of the imaging optics, the image sensor being adapted to convert an optical image into an electric signal; and a second aperture filter arranged in the illumination optics on a plane that is conjugate to the plane on which the first aperture filter is arranged; wherein one of the first or second aperture filter has a circular aperture with a coherence factor that is less than 1 (a<1), and the other has an annular aperture.

2. The optical microscope device according to claim 1, wherein the first aperture filter has a circular aperture with a coherence factor that is less than 1 ($\sigma<1$), and the second aperture filter has an annular aperture.

3. The optical microscope device according to claim 1, wherein the second aperture filter has a circular aperture with a coherence factor that is less than 1 ($\sigma<1$), and the first aperture filter has an annular aperture.

4. The optical microscope device according to claim 1, wherein
the annular aperture is formed as a space interposed between a first non-light-transmissive, disc-shaped member and a second non-light-transmissive member, the second member being arranged on an outer side of the aperture and defining an extension of the aperture, and
a support member that extends from the second member in a manner supporting the first member is arranged in parallel with or at a right angle to a pattern formed on a sample plane.

5. The optical microscope device according to claim 4, wherein the support member includes four support members that support the first member from four directions.

6. The optical microscope device according to claim 1, wherein a relationship between transmission characteristics of the first and second aperture filters is decided so that an average brightness of an optical image formed by the imaging optics is located in a linear region of photoelectric conversion characteristics of the image sensor.

7. The optical microscope device according to claim 1, wherein a light beam, from the illumination optics, is caused to irradiate the sample through an objective lens of the imaging optics.

* * * * *